United States Patent [19]

Leimgruber et al.

[11] 4,073,811

[45] Feb. 14, 1978

[54] PROCESS FOR THE PREPARATION OF ALDEHYDES

[75] Inventors: Willy Leimgruber, Montclair; Donald Herman Valentine, Jr., Westfield, both of N.J.

[73] Assignee: Hoffmann-La Roche Inc., Nutley, N.J.

[21] Appl. No.: 755,695

[22] Filed: Dec. 30, 1976

Related U.S. Application Data

[60] Division of Ser. No. 442,991, Feb. 15, 1974, Pat. No. 4,016,212, which is a continuation-in-part of Ser. No. 340,496, March 12, 1973, abandoned.

[51] Int. Cl.$^2$ .................. C07C 43/30; C07C 41/06
[52] U.S. Cl. .................. 260/611 A; 260/615 AA
[58] Field of Search ........ 260/615 A, 615 AA, 611 A

[56] References Cited

U.S. PATENT DOCUMENTS

| | | | |
|---|---|---|---|
| 2,501,144 | 3/1950 | Saunders | 260/601 R |
| 3,654,309 | 4/1972 | Thomas | 260/332.3 R |
| 3,965,193 | 6/1976 | Goetz | 260/598 |

FOREIGN PATENT DOCUMENTS

| | | | |
|---|---|---|---|
| 1,138,366 | 1/1969 | United Kingdom | 260/615 AD |

OTHER PUBLICATIONS

Thomas, J.A.C.S., 91 3281-3289 (1969).

*Primary Examiner*—Howard T. Mars
*Attorney, Agent, or Firm*—Samuel L. Welt; Bernard S. Leon; William H. Epstein

[57] ABSTRACT

A multi-step process for the preparation of alpha,beta-unsaturated aliphatic aldehydes such as citral by first reacting an allylic alcohol with a butadienyl ether, or a corresponding acrolein derivative or its acetal, including novel intermediates in this process.

1 Claim, No Drawings

PROCESS FOR THE PREPARATION OF ALDEHYDES

CROSS REFERENCE TO RELATED APPLICATIONS

This application is a division of application Ser. No. 442,991 filed Feb. 15, 1974 now U.S. Pat. No. 4,016,212 which is a continuation-in-part of application Ser. No. 340,496 filed Mar. 12, 1973 and now abandoned.

BACKGROUND OF THE INVENTION

The reaction of an allylic primary alcohol with a lower alkoxy butadienyl ether to give alpha-beta unsaturated aldehydes is disclosed in U.S. Pat. No. 3,654,309, Thomas, Apr. 4, 1972. This reaction was presumed to involve three stages which occur in a single step: transetherification of the butadienyl ether with the primary allylic alcohol to give a new butadienyl ether, followed by sequential Claisen and Cope rearrangements of this substance to yield ultimately an alpha-beta unsaturated aldehyde. According to prior workers (Thomas, *J. Amer. Chem. Soc.* 91, 3281 (1969); Cookson and Rogers, *Chem. Commun.* 281 (1972)), this reaction did not follow the course described above when the butadienyl ether is not substituted by an alkyl group on the carbon alpha to the one bearing the alkoxy group. It was also presumed that when butadienyl ethers having such unsubstituted alpha carbon atoms were employed transetherification and the Claisen rearrangement occurred as described above. However, the major and sometimes exclusive product from this reaction appeared to be derived from the Claisen rearrangement product via an undesired rearrangement and could not be converted into the desired alpha-beta unsaturated aldehyde.

SUMMARY OF THE INVENTION

In accordance with the process of this invention, alpha,beta-unsaturated aldehydes having an unsubstituted alpha-carbon atom of the formula:

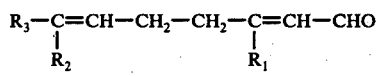

wherein
R$_1$ is lower alkyl;
R$_2$ is lower alkyl; and
R$_3$ is hydrogen, lower alkyl or a linear or branched chain aliphatic hydrocarbon containing from 2 to 8 carbon atoms and from 1 to 2 double bonds;
can be prepared by first reacting a compound of the formula:

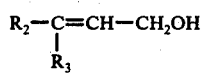

wherein R$_2$, and R$_3$ are as above; with compounds of the formulae:

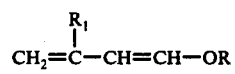

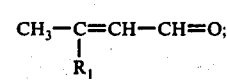

and

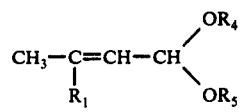

wherein R$_1$ is as above; and —OR, —OR$_4$ and —OR$_5$ form an ether protecting group convertible to hydroxy by hydrolysis;

and then converting the reaction products formed thereby into the aldehyde of formula I.

By the process of this invention, the aldehydes of formula I can be produced in yields as high as 70%.

DETAILED DESCRIPTION OF THE INVENTION

As used herein, the term "lower alkyl" denotes both branched chain and straight chain alkyl groups containing from 1–7 carbon atoms such as methyl, ethyl, propyl, isopropyl, n-butyl, isobutyl, n-hexyl and isohexyl with methyl being preferred. The term "halogen" includes all four halogens such as fluorine, chlorine, bromine, iodine with chlorine and bromine being preferred. The term "alkali metal" includes such metals as sodium, lithium and potassium.

The term "lower alkanoyl" as used through this application designates lower alkanoyl groups containing from 2–7 carbon atoms as acetyl, propionyl, pivalyl, etc., with acetyl being preferred. The term "aryl" designates mononuclear aromatic hydrocarbon groups such as phenyl, tolyl, which can be unsubstituted or substituted in one or more positions with lower alkyl, a halogen, a nitro, a lower alkylenedioxy, or a lower alkoxy substituent and polynuclear aryl groups such as naphthyl, anthryl, phenanthryl, azulyl, etc., which can be substituted with one or more of the above-mentioned groups. The preferred aryl group is phenyl. The term "aroic acid" designates those acids of the formula:

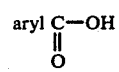

wherein aryl is as defined above.
The preferred aroic acid is benzoic acid.
Where —OR, —OR$_4$ or —OR$_5$ forms a hydrolyzable ether protecting group, any conventional hydrolyzable ether group can be utilized to protect the free hydroxy group. Among the preferred hydrolyzable ethers which form groups —OR, —OR$_4$ or —OR$_5$ are included lower alkoxy, benzyloxy or p-nitrobenzyloxy.

Among the preferred starting materials are those compounds where R$_1$, R$_2$ and R$_3$ are lower alkyl with methyl, ethyl and isobutyl being especially preferred.

Where R$_3$ is a linear or branched chain unsaturated hydrocarbon radical containing from 2 to 8 carbon atoms, the preferred radicals are:
2-hexenyl;
5-ethyl-4-hexenyl;
5-ethyl-2-hexenyl;
2,4-hexadienyl;
3-methyl-3-pentenyl;
4-methyl-3-pentenyl;
3-methylene-4-pentenyl;
3-methyl-2,4-pentadienyl;
3-ethyl-4-methyl-pentenyl;

2-octenyl;
5-heptenyl;
2,3-dimethyl-3-pentenyl;
2,3,4-trimethyl-2,4-pentadienyl;
4-methyl-3-methylene-4-pentenyl;
2-hexenyl;
4-hexenyl;
4-methyl-2,4-pentadienyl;
5-methyl-4-hexenyl; and
5-ethyl-3-hexenyl.

Among these radicals, 4-methyl-3-pentenyl is particularly preferred.

The compounds of formula I are known compounds having valuable odoriferous and/or flavoring properties. Therefore, they are useful as ingredients in the manufacture of perfumes and perfumed products and/or as flavoring agents for foodstuffs and beverages. Among the preferred compounds produced in accordance with this invention are citral, ethyl citral and isobutyl citral.

In accordance with one embodiment of this invention, the compound of formula I is produced from the reaction of the compound of formula II with a butadienyl ether of formula III via the following intermediates:

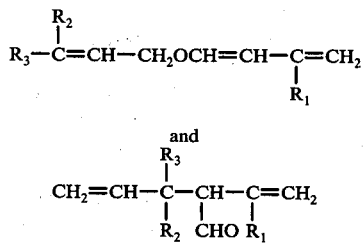

wherein $R_1$, $R_2$ and $R_3$ are as above.

In the first step of the process of this invention, the compound of formula III is reacted with the compound of formula II to produce a compound of the formula VII. In carrying out this reaction, generally, at least 1 mole of the compound of formula III is present per mole of the compound of formula II. Generally, it is preferred to utilize from about 2 to 5 moles of the compound of formula III per mole of the compound of formula II in carrying out this reaction. The excess of the compound of the formula III can serve as the reaction medium in which the reaction of step (a) is carried out. On the other hand, amounts greater than 5 moles, i.e., 15 moles or greater of the compound of formula III per mole of the compound of formula II can be utilized to carry out this reaction. Such large amounts of the compound of formula III are seldom utilized, since no additional benefits are achieved thereby. The reaction medium can, if desired, contain an inert organic solvent as an additional diluent. Any conventional inert organic solvent can be utilized in the reaction medium. Among the preferred inert organic solvents are aliphatic hydrocarbon solvents such as cyclohexane, octane, etc. and aromatic hydrocarbon solvents such as toluene, xylene, etc. This reaction is carried out in the presence of a condensing agent. Any of the conventional acidic condensing agents may be utilized in accordance with this process. These acid condensing agents include mineral acids such as sulfuric acid and phosphoric acid; organic acids such as acetic acid, difluoroacetic acid, trifluoroacetic acid, 2,4-dinitrophenol and o-nitrobenzoic acid, and salts of these acids with metals of groups IA, IIA, IB, IIB, VIB, VIIB and VIII of the Periodic Table such as magnesium, aluminum, calcium, chromium, manganese, silver, cadmium, mercury, iron, cobalt and palladium. Furthermore, alkali metal or ammonium acid salts of mineral acids and strong organic acids such as sodium dihydrogen phosphate, sodium hydrogen sulfate and sodium hydrogen oxalate can also be utilized as the acid condensing agent. Preferred condensing agents are mercuric acetate, phosphoric acid, ammonium dihydrogen phosphate, etc. Mixtures of at least two of the above condensing agents can also be utilized.

It is generally preferred to carry out the reaction of the compound of formula III with the compound of formula II in the presence of a buffering agent. If desired, any conventional buffering agent can be present in this reaction medium utilized to form the compound of formula VII. Among the preferred buffering agents which can be present in this reaction medium are the alkali metal salts of organic monocarboxylic acids which include alkali metal salts of aroic acids such as sodium benzoate and alkali metal salts of lower alkanoic acids such as sodium acetate, sodium propionate, etc. The preferred buffering agent is sodium acetate. In accordance with an especially preferred embodiment of this invention, an acid condensing agent such as mercuric acetate in admixture with a buffering agent such as sodium acetate is utilized in carrying out this reaction.

The condensation of the compound of formula II with the compound of the formula III is carried out at a temperature of 40 degrees centigrade to 100 degrees centigrade. Care must be taken during the course of this reaction to maintain the temperature at 100 degrees centigrade or below. If the temperature of the reaction exceeds 100 degrees centigrade, various side products are formed which decrease the ultimate yield of the compound of formula I.

In the next step of this synthesis, the compound of formula VII is isolated from the reaction mixture. This isolation or separation procedure can be achieved by conventional means such as filtration and distillation. The insoluble part of the catalyst system can be removed from the reaction medium expeditiously via filtration. Where no solvent except for the compound of formula III is utilized, the reaction medium contains the compound of formula VII in admixture with the compound of formula III. These compounds can be easily separated by vacuum distillation since the compound of formula III has a lower boiling point than the compound of formula VII. Any conventional method of vacuum distillation can be utilized. Where there is also present in the reaction medium an inert organic solvent, the compound of formula VII can be isolated from the reaction medium by fractional distillation.

By first forming and isolating the intermediate of formula VII above, the butadienyl ether of formula III above can be converted to the compound of formula I in high yields. It has been unexpectedly discovered that unlike other processes for forming the compound of formula I, the unreacted butadienyl ether of formula III above can be recovered after formation and isolation of the compound of formula VII. In this manner, the recovered butadienyl ether of formula III can be used to react with an additional amount of the compound of formula II to form the compound of formula I. Since the ether of formula III is a relatively expensive material, use of this embodiment of the invention provides a substantial economic improvement in producing the compound of formula I from a butadienyl ether of formula III.

After its isolation, the compound of formula VII can be converted to the compound of formula I by heating at temperatures from 100 degrees centigrade to 230 degrees centigrade. In carrying out this reaction no solvent need be present. However, this reaction can take place in the presence of an inert organic solvent. Any conventional inert organic solvent can be utilized. Among the preferred inert organic solvents are the hydrocarbon solvents such as those mentioned hereinbefore. In carrying out this reaction, a temperature of 100° to 230° C is maintained for a period of at least 3 minutes. Generally, it is preferred to carry out the reaction utilizing a time period of from 3 minutes to 20 hours. However, if desired, time periods of greater than 20 hours can be utilized. If the reaction is stopped after initial heating, analysis of the reaction mixture demonstrates that the compound of formula VIII is produced as an intermediate in the conversion of the compound of formula VII to the compound of formula I. The reaction mixture initially produced upon heating contains the compound of formula VII, the compound of formula VIII and the compound of formula I. Continued heating of this mixture at a temperature of from 100° to 230° C converts both the compound of formula VII and the compound of formula VIII to the compound of formula I.

The compound of formula VIII can also be produced from a compound of the formula:

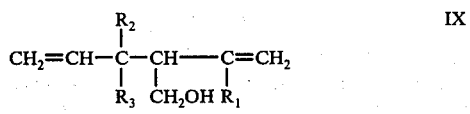

wherein $R_1$, $R_2$ and $R_3$ are as above; by oxidation.

In carrying out the reaction, any conventional method of oxidizing an alcohol to the corresponding aldehyde can be utilized. Among the preferred oxidizing agents are included manganese dioxide, chromate oxidizing agents such as chromium trioxide-pyridine, Jones reagent, etc. In carrying out this reaction, temperature and pressure are not critical and this reaction can be carried out at room temperature and atmospheric pressure. Generally, this oxidation step is carried out in an inert organic solvent. Any conventional inert organic solvent can be utilized for this purpose. Among the preferred organic solvents are included diglyme, chlorinated hydrocarbons such as methylene chloride, chloroform, etc.

The compound of formula VIII can be converted to the compound of the formula I by heating to a temperature of from 100° to 230° C. This reaction is carried out in the same manner as the conversion of a compound of the formula VII to the compound of formula I.

In accordance with another embodiment of this invention, the compound of formula II can be converted to the compound of formula I via an intermediate of the formula:

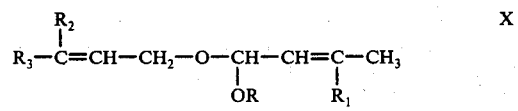

wherein —OR, $R_1$, $R_2$ and $R_3$ are as above.

In preparing the compound of formula X, the compound of formula II is reacted with a compound of formula V. This reaction is carried out in the same manner and under the same conditions that are described in connection with the reaction of a compound of formula II with a compound of formula III except that temperatures of from about 50° to 120° C are utilized. A preferred method of carrying out this reaction is to utilize an acid condensing agent such as mercuric acetate in the presence of a buffering agent such as sodium acetate.

The compound of formula X can also be formed by reacting the compound of the formula II and the compound of formula III in the presence of a complexed palladium chloride or palladium acetate catalyst. In carrying out this reaction, any palladium chloride or palladium acetate catalyst complexed with an organo nitrogen containing ligand such as nitrile, organic amine or pyridine derivative can be utilized. Among the preferred catalysts for use in this reaction are dichloro-bis(-benzonitrile)palladium, and dichloro-o-phenanthroline palladium. In carrying out this reaction, temperatures of from −35° to 50° centigrade can be utilized. In the formation of the compound of formula X by reacting the compound of formula II and the compound of the formula III, no solvent need be present. An excess of the compound of the formula III can serve as the reaction medium for producing the compound of the formula X. On the other hand, if desired, this reaction can be carried out in the presence of an organic solvent. Any conventional inert organic solvent can be utilized for this purpose. Where solvents are utilized, it is generally preferred to utilize aliphatic and aromatic hydrocarbon solvents such as n-octane, toluene, xylene and benzene.

In the reaction of the compound of formula II with the compound of formula V, the compound of formula X is formed in admixture with a small amount of a compound of formula:

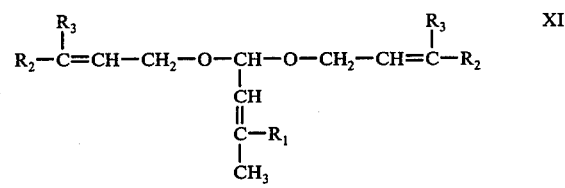

wherein $R_1$, $R_2$ and $R_3$ are as above.

The compound of formula X can be separated from the compound of formula XI by conventional means such as fractional distillation. Both the compound of formula X and the compound of formula XI can be converted to the compound of formula I by similar pyrolysis procedures as seen from the discussion which follows. Hence, the compound of formula X need not be separated from the compound of formula XI or isolated from its reaction mixture in order to carry out the conversion to a compound of formula I.

The conversion of the compounds of formulae X or XI or mixtures thereof to a compound of formula I is effected by pyrolysis. Any conventional means of pyrolysis can be utilized to convert the compounds of formula X or formula XI or mixtures thereof to the compound of formula I. The pyrolysis can take place in the reaction medium utilized to form the compound of formulae X or XI or can take place after isolation of the compound of formula X and the compound of formula XI. In the latter case, pyrolysis can take place in either the liquid or gas phase. However, where the compound of formulae X or XI is not isolated, only liquid phase pyrolysis may be used.

Pyrolysis can take place in either the liquid phase or the gas phase. One of the preferred methods of conducting the pyrolysis is to heat the compound of the formulae X or XI to a temperature of from 120° to 230° C. In carrying out liquid phase pyrolysis, the compound of formulae X or XI can be heated either as a liquid or dissolved in a solvent such as the reaction medium in which it was formed. If desired, a strong acid catalyst can be utilized in carrying out this pyrolysis reaction. Among the preferred acid catalysts for use in carrying out this pyrolysis reaction are p-toluenesulfonic acid, o-nitrobenzoic acid, 2,4-dinitrophenol, sodium hydrogen sulfate, etc. If desired, the reaction medium can contain acidic condensing agents such as disclosed hereinabove such as mercuric acetate, sodium acetate, etc. If the boiling point of the solvent or of the reaction medium falls substantially below the temperature utilized for pyrolysis, it is possible to conduct this pyrolysis under pressure by carrying it out in a sealed tube or in an autoclave.

If the pyrolysis is carried out in the gas phase, the compound of formulae X or XI is subjected to a temperature of from 200° to 400° C. This can be accomplished by passing the compound of formulae X or XI, under an inert atmosphere, on to a column heated to a temperature of from 200° to 400° C. This column can contain a high melting adsorptive material such as pumice, and a solid alkali metal acid salt of a strong acid such as sodium dihydrogen phosphate, etc. By subjecting the compound of formulae X or XI to a heated column containing the alkali metal salt of a strong acid, the compound of formulae X or XI is converted to the compound of formula I.

The compound of formula XI above is also formed by reacting a compound of the formula II with a compound of the formula IV.

In this reaction, at least 2 moles of the compound of formula II are used per mole of the compound of formula IV. Generally, it is preferred to use from about 2 moles to 10 moles of the compound of formula II per mole of the compound of formula IV. If desired, amounts greater than 10 moles of the compound of formula II can be present, i.e., 30 moles or greater of the compound of formula II per mole of the compound of formula IV. This reaction can be carried out in the presence of a condensing agent and a dehydrating agent. Any conventional condensing agent can be utilized. These include mineral acids such as dry hydrogen chloride, sulfuric acid, phosphoric acid, organic acids such as p-toluenesulfonic acid, o-nitrobenzoic acid, and 2,4,6-trinitrophenol, and ammonium, alkali metal acid salts and alkaline earth metal salts of strong organic acids such as calcium sulfate, sodium dihydrogen phosphate, ammonium sulfate, ammonium nitrate, ammonium chloride, etc. Substances such as calcium sulfate, calcium chloride, etc., may be used as both the condensing agent and dehydration agent. In carrying out this reaction, any conventional dehydrating agent can be utilized. Among the preferred dehydrating agents which can be utilized to remove water formed by this condensation are included molecular sieves, sodium sulfate, magnesium sulfate, calcium chloride, etc. The molecular sieves contain metal oxides which are acid anhydrides. In view of this fact, the molecular sieves can be utilized as both the dehydrating agent and condensing agent in this reaction. In forming the compound of formula XI, no solvent need be present. The excess amount of the compound of formula II can serve as the reaction medium. On the other hand, this reaction can be carried out in the presence of an inert organic solvent. Any conventional inert organic solvent can be utilized, if desired, in carrying out this reaction. Among the preferred inert organic solvents are included aliphatic aromatic hydrocarbon solvents such as those mentioned hereinbefore. In carrying out this reaction, temperature and pressure are not critical and this reaction can be carried out at room temperature and atmospheric pressure. On the other hand, elevated or reduced temperatures can be utilized. Generally, it is preferred to carry out this reaction at a temperature of from 0° to about 80° C.

The compound of formula XI can be converted to the compound of formula I without the need for isolating this compound from the reaction mixture in which it is formed. On the other hand, the compound of formula XI can be isolated from the reaction mixture by conventional means such as fractional distillation under vacuum and converted directly to the compound of formula I. The conversion of the compound of the formula XI to the compound of formula I is carried out by pyrolysis. Any conventional method of pyrolysis such as those mentioned hereinbefore can be utilized.

The invention is further illustrated by the following examples which are illustrative but not limitative thereof. All temperatures are in degrees centigrade.

EXAMPLE 1

To a mixture of 12.0 g. of 3-methyl-but-2-en-1-ol with 30.0 g. of methyl (3-methyl-1,3-butadienyl) ether under argon was added 3.0 g. of mercuric acetate and 3.0 g. of sodium acetate.

The resulting two-phase system was heated to 45 degrees centigrade for four hours under argon. After four hours, the mercury salts had dissolved and the solid residue was essentially pure sodium acetate which was removed by filtration. The filtrate was distilled under reduced pressure. A low-boiler fraction of 24 g. was shown by vapor phase chromatography to be about 90% methyl (3-methyl-1,3-butadienyl) ether, contaminated with some 3-methyl-but-2-en-1-ol (prenol). A second fraction containing 12.2 g. of 92–94% pure 3-methyl-but-2-enyl (3-methyl-1,3-butadienyl) ether, b.p. 60 degrees centigrade (0.2 mmHg.), was obtained. To the low-boiler fraction was added 7 g. of methyl (3-methyl-1,3-butadienyl) ether, 12.0 g. of 3-methyl-but-2-en-1-ol, 3.0 g. of mercuric acetate and 3.0 g. of sodium acetate. The mixture was heated as above to yield 12.1 g. of 3-methyl-but-2-enyl (3-methyl-1,3-butadienyl) ether together with a low-boiler fraction of 23 g. of 90% pure methyl (3-methyl-1,3-butadienyl) ether mixed with some prenol. This was mixed with 7 g. of methyl (3-methyl-1,3-butadienyl) ether, 12.0 g. of 3-methyl-but-2-en-1-ol, 3.0 g. of mercuric acetate and 3.0 g. of sodium acetate, to give again 12.1 g. of 3-methyl-but-2-enyl-(3-methyl-1,3-butadienyl) ether. The combined yield of 3-methyl-but-2-enyl-(3-methyl-1,3-butadienyl) ether is 50% based on 3-methyl-but-2-en-1-ol and 92% based on unrecovered methyl (3-methyl-1,3-butadienyl) ether.

EXAMPLE 2

A mixture of 30 g. of 3-methyl-but-2-enal dimethyl acetal, 15 g. of 3-methyl-but-2-en-1-ol, 1.3 g. of sodium acetate and 4.0 g. of mercuric acetate was heated under argon for 16 hours at 120 degrees centigrade. After cooling and filtering, vacuum distillation gave some low-boilers followed by 15.8 g. of 1-methoxy-1-(3-methyl-but-2-enoxy)-3-methyl-2-butene and in a later fraction 1.2 g. of 1,1-bis-(3-methyl-but-2-enoxy)-3-methyl-2-butene.

EXAMPLE 3

A mixture of 2.0 g. of 3-methyl-but-2-en-1-ol with 5.0 g. of methyl (3-methyl-1,3-butadienyl) ether was cooled to −78 degrees centigrade under argon and 100 mg. of dichloro-bis-(benzonitrile) palladium (II) was added.

The stirred reaction mixture was then allowed slowly to warm to −15° centigrade when an abrupt color change from yellow to brown occurred and analysis of the mixture by vapor phase chromatography indicated that 1-methoxy-(3-methyl-but-2-enoxy)-3-methyl-2-butene had begun to form. The mixture was kept at −15° centigrade for 45 minutes, then 300 mg. of triphenylphosphine was added to convert the palladium complexes to dichloro-bis-(triphenylphosphine) palladium (II), which was removed by filtration. Vacuum distillation of the filtrate gave 1.4 g. of 1-methoxy-1-(3-methyl-but-2-enoxy)-3-methyl-2-butene; b.p. 80°–85° C. (1 mmHg).

EXAMPLE 4

A mixture of 30 g. of 3-methylbut-2-enal, 70 g. of 3-methyl-but-2-en-1-ol, 0.7 g. of ammonium nitrate and 20 g. of Linde 4A Molecular Seives[1] was stirred at 25° C. and formation of 1,1-bis-(3-methyl-but-2-enoxy)-3-methyl-2-butene was followed by vapor phase chromatography. When formation of 1,1-bis(3-methylbut-2-enoxy)-3-methyl-2-butene stopped after about 72 hours, 20 g. of sodium carbonate was added, the solution was stirred for 20 minutes, then filtered and vacuum distilled. By vacuum distillation there was obtained 37 g. of low boilers (a mixture of 3-methylbut-2-en-1-ol and 3-methylbut-2-en-1-al in about 5:1 parts by volume ratio) and 31.2 g. of 1,1-bis-(3-methylbut-2-enoxy)-3-methyl-2-butene. There was 3 g. of distillation residue.

[1] A mixture of 1 part by weight of sodium oxide, 1 part by weight aluminum oxide and 2 parts by weight $SiO_2.H_2O$.

EXAMPLE 5

14 g. of 3-methyl-but-2-enyl (3-methyl-1,3-butadienyl) ether was heated to 200° centigrade for 30 minutes in an evacuated sealed ampoule. Vacuum distillation of the reaction mixture gave 12.4 g. of ca. 95% pure citral (88% yield), b.p. 60° C (0.1 mmHg.).

This pyrolysis was followed by analysis by vapor phase chromatography of samples taken at regular intervals from a 0.200 ml. sample heated at 180° C for a total of 5 minutes. The vapor phase chromatography date indicated that 3-methyl-but-2-enyl (3-methyl-1,3-butadienyl) ether was converted first to 2-isopropenyl-3,3-dimethyl-pent-4-enal which was then converted to citral.

EXAMPLE 6

A solution of 1,1-bis-(3-methyl-but-2-enoxy)-3-methyl-but-2-ene (10.0 g. 41.3 mmol.) and 2,4-dinitrophenol (0.17 g., 1.01 mmol.) in toluene (300 ml.) was refluxed for 45 hours. After cooling to room temperature, the toluene solution was washed with 4 × 50 ml. of saturated $NaHCO_3$ solution, 2 × 100 ml. of saturated NaCl solution and dried with anhydrous NaOAc. The toluene was removed by distillation at 20 mm and an oil bath temperature of 55°–60° C. The residue was diluted with diethyl ether and washed with 3 × 50 ml. of saturated aqueous NaCl solution. The ether layer was then dried (anhydrous NaOAc) and concentrated under reduced pressure. Distillation of the residue through a short column gave pure citral.

EXAMPLE 7

Chromium trioxide (2.0 g.) was added to a stirred solution of 3.17 g. of pyridine in 50 ml. of methylene chloride. The mixture was stirred for 15 minutes at 25° C. 2-Isopropenyl-3,3-dimethylpent-4-en-1-ol (0.510 g.) was then added all at once. The resulting mixture was stirred for 10 minutes. The methylene chloride was decanted and the residue was washed with ether. Ether and methylene chloride were combined and washed with 3× 35 ml. of 5% aqueous sodium hydroxide, 35 ml. of 5% aqueous hydrochloric acid, 35 ml. of 5% sodium bicarbonate, 35 ml. of saturated aqueous sodium chloride, dried over magnesium sulfate and evaporated under aspiration suction. Distillation of the residue under vacuum gave 0.375 g. of 2-isopropenyl-3,3-dimethyl-4-pentenal-1; b.p. 80°–85° C (15 mmHg.) with $v_{CO} = 1720$ cm$^{-1}$.

EXAMPLE 8

The compound: 1,1-bis-(3-methyl-but-2-enoxy)-3-methyl-2-butene; was converted to citral by vacuum pyrolysis.

The apparatus used in this vacuum pyrolysis consisted of a vertical cylindrical glass tube which was 25 mm in diameter and 130 cm long, enclosed in an oven made of a steel pipe wrapped with a heating coil and then again with asbestos paper. The top of the column was connected via a 24/40 joint to a pressure adjusted dropping funnel so that the compound could be added dropwise to the top of the column. The pyrolysate was collected at the bottom of the column in a 1,000 ml., 3-neck flask connected by another 24/40 joint to the vertical glass tube. This receiving flask was cooled in dry ice-acetone and contained ca. 100 ml. of frozen aqueous $NaHCO_3$ solution to prevent acid catalyzed combinations of methanol with the various pyrolysis reactions. The receiving flask was connected to a vacuum pump via two dry ice-acetone traps. Pyrolysis temperatures were determined by inserting the probe of a thermocouple between the steel and glass pipes of the pyrolysis apparatus. Temperatures reported are thus not necessarily actual column temperatures.

Sodium dihydrogen phosphate was dried by slowly heating it under vacuum to 220 degrees centigrade, agitating it occasionally to prevent lump formation, then grinding a dry atmosphere and briefly heating again under vacuum. Dried $NaH_2PO_4$ granules were mixed with an equal volume of 4–8 mesh pumice and then poured onto the column which was heated overnight at 325 degrees centigrade under vacuum.

Once the packed column has been heated to 325 degrees centigrade, it may be used repeatedly and allowed contact with air without deleterious effect provided it is not allowed to cool. On cooling the column packing congeals to a solid mass which could not be removed from the column but which still was catalytically active.

17.5 g. of 1,1-bis-(3-methyl-but-2-enoxy)-3-methyl-but-2-ene was placed in the dropping funnel of the apparatus described above and dripped onto the column at 350° C and 2 mmHg. pressure measured at the vacuum pump over a 6-hour period. The collection flask was a 1,000 ml. three-neck flask, connected to the column and the vacuum pump, cooled in a dry ice-acetone bath and containing 100 ml. of frozen saturated aqueous sodium bicarbonate.

After pyrolysis was complete, the pyrolysate (16.3 g.) was allowed to warm to 25° C and was extracted with 2 × 200 ml. of diethyl ether. The ether extracts were washed with saturated aqueous sodium chloride, dried over $Na_2CO_3$, filtered, evaporated on the steambath and distilled through a Vigreaux column to afford 4.1 g. of citral.

EXAMPLE 9

The mixture of 2.0 g. of 1-methoxy-1-(3-methylbut-2-enoxy)-3-methyl-2-butene, 20 mg. of $NaH_2PO_4$ and 10 ml. of heavy mineral oil having a boiling point of over 350° C. was deaereated by bubbling argon through it for 10 minutes, then heated for 50 minutes at 200° C. The yellow reaction mixture was then cooled to room temperature and 100 mg. of $NaHCO_3$ was added. Vacuum distillation then gave 1.2 g. of low boilers and 0.70 g. of citral.

EXAMPLE 10

The compound 3-methyl-but-2-enyl (3-methyl-1,3-butadienyl) ether (3 ml.) was heated under argon in an oil bath at 180° C. for 3 minutes, then quickly cooled to 25° C. by immersing in ice. The pyrolysate was subjected to preparative vapor phase chromatography on a column. By this chromatography there was isolated 2-isopropenyl-3,3-dimethyl-4-pentenal.

EXAMPLE 11

The aldehyde, 2-isopropenyl-3,3-dimethyl-4-pentenal-1 (200μl) was placed in a tube which was evacuated and sealed under vacuum, then immersed 10 minutes in 180° C. oil bath to produce citral (85% pure).

EXAMPLE 12

In a 250 ml. three-neck flash, fitted with a mechanical stirrer, vent and a serum cap were placed 93 g. (1.08 mol.) of prenol (3-methylbut-2-en-1-ol) and 40 g. (0.476 mol) of prenal (3-methyl-but-2-en-1-al). The resulting solution was degassed with nitrogen, sealed with the serum cap, stirring begun and a water bath (15°) was placed under the reaction flask. Then 60 g. of powdered 5A molecular sieves[1] were rapidly added. After about 40 minutes the initial exothermicity has subsided and the water bath was removed and stirring continued at room temperature. The reaction was monitored by vpc (vapor phase chromatography) and when vpc indicated that the reaction had ceased, the reaction mixture was filtered. The solids were washed thoroughly with 6 × 150 ml. of hexane to leave 67.9 g. of used molecular sieves. The combined filtrates were concentrated under reduced pressure (20 mmHg at 25°) to give 135.75 g. of a light yellow liquid. Distillation at 17 mmHg and an oil bath temperature of 60°–75° gave 28.95 g. of recovered prenol and prenal (8:1 parts by volume). (The dry ice trap yielded 12.6 g. of hexane containing traces of prenal.) Continued distillation at 0.50 mmHg and a bath temperature of 45°–55° gave an additional 11.19 g. of prenol. Flash distillation of the residue (77.24 g.) 0.015 mmHg at an oil bath temperature of 95°–97° gave 75.4 g. of 1,1-bis-(3-methylbut-2-enoxy)-3-methylbut-2-ene as a clear liquid, purity 95% or better as determined by vpc. This represents a conversion of 67% and a yield of 97% based on consumed prenol and 73% based on consumed prenal.

[1]The sieves contained 0.2 parts by weight sodium oxide, 0.8 parts by weight calcium oxide, 1 part by weight aluminum oxide and 2 parts by weight $SiO_2.H_2O$.

EXAMPLE 13

In a 250 ml. three-neck flask, fitted with a mechanical stirrer, stopper and serum cap was placed 50 g. (0.581 mol.) of prenol and 13 g. (0.155 mol.) of prenal. This solution was degassed with nitrogen and 57 g. of powdered $CaSO_4$ was added. The resulting mixture was stirred at room temperature for 100 hours. The solids were removed by filtration and washed thoroughly with 4 × 100 ml. of anhydrous diethyl ether to leave 60.42 g. of recovered $CaSO_4$. The filtrates were combined and concentrated (20 mmHg and a bath temperature of 26°) to give 63.3 g. of a colorless liquid. Distillation at 20 mmHg and an oil bath temperature of 65°–70° gave 33.66 g. of recovered prenol and prenal (30.76 g. prenol + 2.9 g. prenal; ratio ca. 10:1 parts by volume). Flash distillation of the residue (25.54 g.) at 0.015 mmHg and an oil bath temperature of 95°–97° gave 25.0 g. 1,1-bis-(3-methylbut-2-enoxy)-3-methylbut-2-ene as a clear liquid, purity 95% or better as determined by vpc. This represents a conversion of 68% and a yield of 94% based on consumed prenol and 88% based on consumed prenal.

EXAMPLE 14

In a 500 ml. one-neck flask, fitted with a reflux condenser and nitrogen inlet was placed 10.0 g. (41.3 mmol.) of the 1,1-bis-(3-methylbut-2-enoxy)-3-methylbut-2-ene in 300 ml. of toluene containing 0.17 g. (1.01 mmol.) of 2,4-dinitrophenol. The resulting solution was refluxed under nitrogen for 45 hours then cooled to room temperature and washed with 4 × 50 ml. of saturated aqueous $NaHCO_3$ solution and 2 × 100 ml. of saturated aqueous NaCl solution. The toluene solution was dried (anhydrous NaOAc) and the toluene removed by distillation at 20 mmHg and a bath temperature of 55°–60° C. The residue was diluted with diethyl ether and washed with 3 × 50 ml. of saturated aqueous NaCl solution. The ether layer was dried (anhydrous NaOAc) and concentrated under reduced pressure. Distillation of the residue through a short column gave 3.9 g. of pure (98%+) citral, b.p. 51°–54° C. at 0.4 mmHg (61%).

EXAMPLE 15

In a 1l. single-necked flask, fitted with a reflux condenser and nitrogen inlet was placed 30.0 g. (0.126 mol.) of 1,1-bis-(3-methylbut-2-ene and 500 ml. of toluene containing 0.5 g. (0.0027 mol.) of 2,4-dinitrophenol. This solution was refluxed under nitrogen for 32 hours and then cooled to room temperature. The reaction solution was washed with 3 × 100 ml. of 0.1 N aqueous NaOH solution followed by washing with 2 × 100 ml. of saturated NaCl solution. The combined aqueous washings were back extracted with 1 × 100 ml. of diethyl ether, this ether extract was washed with 1 × 50 ml. of saturated aqueous NaCl solution and then combined with the toluene solution. The combined organic solutions were treated with activated charcoal and then dried ($MgSO_4$) and concentrated to give 25.4 g. of an orange liquid. Distillation through a short-path distillation apparatus at 0.3 mmHg gave two fractions:

1. 3.9 g. b.p. 47°–51° analyzing for 88% citral and 12% low boilers;

2. 10.6 g. b.p. 51°–53° analyzing for 96% citral and 4% low boilers.

The residue from this distillation contained small amounts of citral and 1,1-bis-(3-methylbut-2-enoxy)-3-methylbut-2-ene. The distillation fractions were redistilled at 0.30 mmHg to give 12.9 g. of pure (96%+) citral, b.p. 52°–54°, 0.3 mmHg (67%).

EXAMPLE 16

In a 50 ml. one-neck flask was placed 5.5 g. (0.0422 mol.) of 1,1-dimethoxy-3-methyl-2-butene and 10.0 g. (0.116 mol.) of prenol and 0.40 g. (0.002 mol.) of 2,4-dinitrophenol. The resulting solution was degassed with nitrogen and sealed with a serum cap and stirred at room temperature for 76 hours. The reaction solution was then diluted with 100 ml. of hexane and washed with 3 × 100 ml. of 1.0 N aqueous NaOH solution and 2 × 100 ml. of saturated aqueous NaCl solution. The combined water washings were back with extracted 1 × 50 ml. of hexane. The combined hexane solutions were dried ($Na_2SO_4$) and concentrated to give 9.0 g. of crude product. Distillation of 8.3 g. at 20 mmHg and a bath temperature of 55°–60° gave 1.48 g. of prenol. Continued distillation initially at 0.20 mmHg gave 2.43 g. of 1-methoxy-1-(3-methylbut-2-enoxy)-3-methyl-2-butene (b.p. 40°–45° at 0.02 mmHg) and finally at 0.050 mmHg gave 3.29 g. of 1,1-bis-(3-methylbut-2-enoxy)-3-metylbut-2-ene (b.p. 70°–75° at 0.050 mmHg).

EXAMPLE 17

In a 100 ml. one-neck flask equipped with stirrer, nitrogen inlet and reflux condenser was placed 5.72 g. (0.0132 mol. of 1-methoxy-1-(3-methylbut-2-enoxy)-3-methyl-2-butene and 0.0138 mol of 1,1-bis-(3-methylbut-2-enoxy)-3-methylbut-2-ene, 40 ml. of toluene containing 0.030 g. (0.00016 mol.) of 2,4-dinitrophenol. The reaction solution was heated to reflux for 80 hours, cooled to room temperature and washed with 3 × 20 ml. of 2 N aqueous NaOH solution, and 1 × 20 ml. of saturated aqueous NaCl. The toluene solution was treated with activated charcoal, dried ($Na_2SO_4$) and concentrated to give, after flash distillation at 0.25 mmHg at a bath temperature of 95°, 3.49 g. of a yellow liquid. Distillation at 0.4 mmHg gave 2.48 g. of citral, b.p. 59°–61° at 0.4 mmHg (60%).

EXAMPLE 18

Preparation of 3-methyl-1,1-bis(3,7-dimethyl-2,6-octadienoxy)-2-butene

In a 25 ml. one-neck flask was placed 9.24 g. (0.0599 mol.) of a mixture of geraniol and nerol and 1.90 g. (0.0226 mol.) of prenal. The resulting solution was degassed with nitrogen and 3 g. of powdered molecular sieves 5A (as described in Example 12) were added rapidly and the flask sealed with a serum cap. The reaction mixture was then stirred at room temperature for 3 hours and the solids removed by filtration and washed thoroughly with 3 × 15 ml. of anhydrous diethyl ether. The combined filtrates were concentrated at 20 mmHg and 26° to give 10.0 g. of a colorless liquid. The unreacted geraniol-nerol 3.24 g. was removed by distillation at 0.10 mmHg and an oil bath temperature of 70°–75° to leave 5.8 g. of 3-methyl-1,1-bis(3,7-dimethyl-2,6-octadienoxy)-2-butene. This represents a conversion of 68% and a yield of 79% based on consumed alcohol.

EXAMPLE 19

Preparation of 1,1-bis(3-methyl-2-butenoxy)-2-butene

In a 100 ml. one-neck flask was placed 17.05 g. (0.198 mol.) of prenol and 5.5 g. (0.0785 mol.) of crotonaldehyde. The resulting solution was degassed with nitrogen and 11.8 g. of powdered molecular sieves (as in Example 12) were added rapidly and the flask sealed with a serum cap and stirred at room temperature for 46 hours. The solids were removed by filtration and washed thoroughly with hexane to leave 13.3 g. of recovered molecular sieves. The combined filtrate and washings were concentrated (20 mmHg and 30°) to leave 18.9 g. of a light yellow liquid. Distillation of the 18.9 g. of 20 mmHg and a bath temperature of 65°–70° gave 9.0 g. of recovered crotonaldehyde and prenol (1:5) leaving 7.4 g. of pure 1,1-bis(3-methyl-2-butenoxy)-2-butene. This represents a conversion of 68% and a yield of 97% based on prenol and 94% based on crotonaldehyde.

EXAMPLE 20

In a 25 ml. one-neck flask, fitted with stirrer, nitrogen inlet and reflux condenser was placed 2.0 g. (0.0089 mol.) of 1,1-bis(3-methyl-2-butenoxy)-2-butene, in 20 ml. of toluene containing 0.110 g. (0.0006 mol.) of 2,4-dinitrophenol. The resulting solution was heated to reflux for 88 hours, cooled to room temperature and washed with 3 × 15 ml. of 2 N NaOH solution and 1 × 15 ml. of saturated aqueous NaCl solution. The toluene solution was dried ($Na_2SO_4$) and concentrated. The residue was flash distilled at 0.4 mmHg and an oil bath temperature of 90° to give 0.41 g. of 7-methyl-2,6-octadienal. Fractional distillation of (0.41 g.) at 12 mmHg gave 7-methyl-2,6-octadienal, 0.32 g., b.p. 82°–84° at 12 mmHg.

We claim:

1. A process for forming an acetal of the formula:

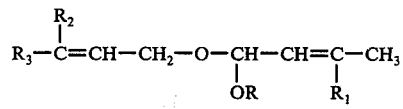

wherein $R_1$ and $R_2$ are lower alkyl; $R_3$ is hydrogen, lower alkyl; and —OR is lower alkoxy or benzyloxy; comprising reacting at a temperature of from −35° to 50° C. an alcohol of the formula:

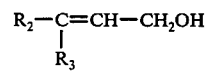

wherein $R_2$ and $R_3$ are as above;
with a butadienyl ether of the formula:

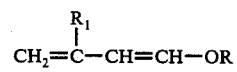

wherein $R_1$ and R are as above; said reaction being carried out in the presence of a dichloro-bis(benzonitrile) palladium or dichloro- phenanthroline palladium.

* * * * *